United States Patent [19]
Colle et al.

[11] Patent Number: 5,322,848
[45] Date of Patent: Jun. 21, 1994

[54] N-ACYL-SUBSTITUTED AZACYCLIC COMPOUNDS, PROCESSES FOR THEIR PREPARATION, AND THEIR USE AS PHARMACEUTICALS

[75] Inventors: Robert Colle; Giulio Dondio; Giuseppe Giardina; Lorenzo Leurini; Vittorio Vecchietti, all of Milan, Italy

[73] Assignee: Dr. Lo Zembeletti S.p.A., Milan, Italy

[21] Appl. No.: 859,388

[22] PCT Filed: Nov. 20, 1990

[86] PCT No.: PCT/EP90/02011
§ 371 Date: May 22, 1992
§ 102(e) Date: May 22, 1992

[87] PCT Pub. No.: WO91/08206
PCT Pub. Date: Jun. 13, 1991

[30] Foreign Application Priority Data

Nov. 24, 1989 [GB] United Kingdom ............... 8926561
Feb. 12, 1990 [GB] United Kingdom ............... 9003137

[51] Int. Cl.$^5$ ............... A61K 31/47; A61K 31/445; C07D 217/06; C07D 401/06
[52] U.S. Cl. ............... 514/307; 514/318; 514/320; 514/324; 514/326; 546/146; 546/193; 546/196; 546/202; 546/208; 546/209; 546/226; 546/227
[58] Field of Search ............... 540/476, 481, 484, 544; 544/60, 130; 546/139, 143, 146, 193, 197, 198, 195, 196, 202, 200, 205, 206, 208, 209, 226, 227; 514/318, 307, 320, 326, 324

[56] References Cited

U.S. PATENT DOCUMENTS

| | | | |
|---|---|---|---|
| 4,954,509 | 9/1990 | Vecchietti | 546/143 |
| 4,999,359 | 5/1991 | Vecchietti | 546/120 |
| 5,030,649 | 7/1991 | Vecchietti | 548/568 |
| 5,089,507 | 2/1992 | Vecchietti | 546/227 |

FOREIGN PATENT DOCUMENTS

| | | |
|---|---|---|
| 0330461 | 2/1989 | European Pat. Off. |
| 0330467 | 2/1989 | European Pat. Off. |
| 0330469 | 2/1989 | European Pat. Off. |
| 0366327 | 10/1989 | European Pat. Off. |

OTHER PUBLICATIONS

Gottschlich et al "Preparation of 2-Acyl-1-Pyrrolidinomethyl 1,2,3,4-Tetrahydro Isoquinolines and Analogs and Drugs" CA 113:211862x (1990).

T. Mukaiyama et al., "Enantioface-Differentiating (Asymmetric) Addition of Alkyllithium and Dialkylmagnesium to Aldehydes by Using (2S,2'S)-2-Hydroxymethyl-1-((1-alkylpyrrolidin-2-yl)-methyl)pyrrolidines as Chiral Ligands", *J. Am. Chem. Soc.*, vol. 101, No. 6, 1979, pp. 1455–1460.

*Primary Examiner*—C. Warren Ivy
*Assistant Examiner*—Celia Chang
*Attorney, Agent, or Firm*—Charles M. Kinzig; Stephen Venetianer; Edward T. Lentz

[57] ABSTRACT

A compound, or solvate or salt thereof, of formula wherein

A is

R is (Abstract continued on next page.)

-continued
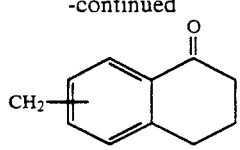
$R_1$ is hydrogen, halogen, or $C_{1-6}$ alkyl;
$R_2$ and $R_3$ are hydrogen or $C_{1-6}$ alkyl;
$R_5$ together with $R_4$ forms a —$(CH_2)_2$— group optionally substituted by one or two $C_{1-6}$ alkyl;
W is halogen or when A is gem-dimethyl substituted piperidine, is OH;
a is 1 or 2,
useful in the treatment of pain.
13 Claims, No Drawings

N-ACYL-SUBSTITUTED AZACYCLIC COMPOUNDS, PROCESSES FOR THEIR PREPARATION, AND THEIR USE AS PHARMACEUTICALS

This invention is concerned with novel substituted azacyclic derivatives, processes for their preparation, and their use in medicine, particularly as analgesics.

Compounds which are kappa-receptor agonists act as analgesics through interaction with kappa opioid receptors. the advantage of kappa-receptor agonists over the classical $\mu$-receptor agonists, such as morphine, lies in their ability to cause analgesia while being devoid of morphine-like behavioural effects and addiction liability.

EP-A-330461, 330467 AND 330469 (Glaxo Group Ltd) disclose groups of azacyclic derivatives which are stated to exhibit kappa-receptor agonism, and which are said to be of potential therapeutic utility in the treatment of pain and cerebral ischaemia.

A novel class of structurally related substituted azacyclic derivatives has now been discovered which also exhibit potent kappa-receptor agonism without some of the undesirable behavioural effects of morphine and morphine analogues.

Furthermore, this novel class of derivatives tend to show improved duration of action over corresponding unsubstituted azacyclic derivatives, while maintaining effective analgesic activity.

The novel class of derivatives also possess diuretic activity which indicates that they are of potential use in the treatment of hyponatraemic disease states in mammals.

The novel class of derivatives are also of potential use in the treatment of cerebral ischaemia.

According to the present invention there is provided a compound, or a solvate or salt thereof, of formula (I):

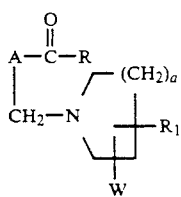

in which W, which may be attached to the same or different carbon atom as $R_1$, is hydroxy, $C_{1-6}$ alkoxy (preferably methoxy), halogen (preferably fluorine), thiol, $C_{1-6}$ alkylthio, hydroxy $C_{1-6}$ alkyl, methylidene, hydroxycarbonyl, aminocarbonyl, $C_{1-3}$ alkoxycarbonyl, $NHR_{1a}$ or $NHCOR_{1a}$ where $R_{1a}$ is H or $C_{1-6}$ alkyl;

$R_1$ is hydrogen, halogen (preferably fluorine), $C_{1-6}$ alkyl (preferably methyl) or together with W forms a keto-group or a cyclic ether or thioether containing from 1 to 4 carbon atoms;

A represents

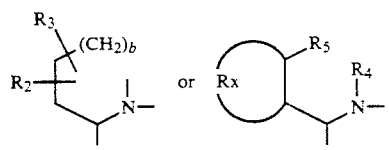

in which each of $R_2$ and $R_3$, which may be attached to the same or different carbon atom, is hydrogen, $C_{1-6}$ alkyl, hydroxy, thiol, $C_{1-6}$ alkoxy, $C_{1-6}$ alkylthio or halogen (preferably fluorine);

$R_4$ is $C_{1-6}$ alkyl;

$R_5$ is hydrogen or together with $R_4$ forms a $-(CH_2)_c-$ group optionally substituted by one or two $C_{1-6}$ alkyl groups and attached to the same or different carbon atom;

$R_x$ is the remainder of an optionally substituted single or fused ring heterocyclic group, preferably having aromatic character, containing from 5 to 12 ring atoms and comprising up to four hetero-atoms in the or each ring selected from oxygen, nitrogen and sulphur;

or $R_x$ is the remainder of an optionally substituted phenyl group;

a is 1 or 2, b is 1, 2 or 3; c is 1, 2 or 3;

and RCO, which is linked to the nitrogen atom of the group A, is an acyl group in which the group R contains a substituted or unsubstituted carbocyclic aromatic or heterocyclic aromatic ring, with the provisos that:
i) When A represents

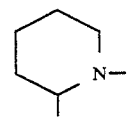

, R represents a tetralone moiety, or W is halogen or $C_{1-6}$ alkoxy, or $R_1$ is other than hydrogen or a keto group with W;

ii) When $R_2$ is $C_{1-6}$ alkyl, $R_3$ is other than hydrogen;

iii) When $R_x$, $R_4$ and $R_5$ together form an unsubstituted tetra hydroisoquinoline group, R represents a tetralone moiety or $R_1$ is other than hydrogen or a keto group with W, or W is halogen or $C_{1-6}$ alkoxy;

iv) When $R_x$, $R_4$ and $R_5$ together form a substituted tetrahydro isoquinoline group, substitution only occurs in the $-(CH_2)_3-$ group formed by $R_4$ and $R_5$.

Preferably, the R tetralone moiety is of formula (IIa), (IIb), (IIc) or (IId) as hereinafter defined.

Preferably, W and $R_1$ are attached to the same carbon atom on the azacyclic ring, in the 3-position with respect to the nitrogen.

Preferably, one of $R_2$ and $R_3$ is halogen (preferably fluorine), $C_{1-6}$ alkoxy, thiol, $C_{1-6}$ alkylthio, or both $R_2$ and $R_3$ are other than hydrogen. In a particularly preferred embodiment, $R_2$ and $R_3$ are attached to the same carbon atom in the azacyclic ring. In the latter case, preferred groups are alkyl, thereby providing a gem di-alkyl substitution pattern.

Examples of W are hydroxy, fluoro and methoxy, and examples of $R_1$ are hydrogen, methyl and fluoro.

It is also preferred that when $R_x$ forms the remainder of a phenyl ring and $R_4$ and $R_5$ form a $-(CH_2)_3-$ group, the latter is substituted, particularly by two $C_{1-6}$ alkyl groups on the same carbon atom of the $-(CH_2)_3-$ group. A particularly preferred substituent is methyl.

When used herein to define the RCO group, the term 'carbocyclic aromatic group' includes single or fused rings, having 6 to 12 ring carbon atoms, and the term 'heterocyclic aromatic group' includes single or fused rings having 5 to 12 ring atoms, comprising up to four hetero-atoms in the or each ring, selected from oxygen, nitrogen and sulphur.

When the carbocyclic or heterocyclic group is a fused two ring system, one or both rings may be aromatic in character.

Suitably, one of the rings is aromatic and the other is non-aromatic.

Examples of $R_x$ as a heterocyclic group are single ring systems, such as thienyl, furyl, pyrryl, imidazolyl, pyrazolyl, thiazolyl, and pyridyl, and when $R_x$ forms a fused ring system, examples are benzofuranyl, benzothienyl, indolyl and quinolyl. Examples of optional substituents for $R_x$ are one or more of $C_{1-6}$ alkyl, preferably methyl, hydroxy, $C_{1-6}$ alkoxy or halogen.

The group R preferably has the formula (II):

$$-(CHR_7)_n-X-Ar\begin{matrix}(R_6)_m\\(R_6^a)_{m'}\end{matrix}\quad\text{(II)}$$

in which
  n is 0, 1 or 2;
  m is 0, 1 or 2;
  m' is 0, 1 or 2, provided m + m' ≤ 3
  X is a direct bond, or O, S or $NR_8$ in which $R_8$ is hydrogen or $C_{1-6}$ alkyl,
Ar is a substituted or unsubstituted carbocyclic or heterocyclic group,
  each of $R_6$ and $R_6^a$ is $C_{1-6}$ alkyl, $C_{2-6}$ alkenyl, $C_{2-6}$ alkynyl, $C_{1-6}$ haloalkyl, $C_{2-6}$ haloalkenyl, $C_{2-6}$ haloalkynyl, optionally substituted phenyl or heterocyclyl, optionally substituted phenyl $C_{1-6}$ alkyl, hydroxy, $C_{1-6}$ alkoxy, thiol, $C_{1-6}$ alkylthio, $C_{1-6}$ haloalkoxy, $C_{1-6}$ haloalkylthio, halogen, $NO_2$, CN, $CF_3$, $-OCF_3$, $-OCHF_2$, $-OCF_2CF_2H$, $-OCCl_2CF_3$, $-COOR_9$, $-CONR_{10}R_{11}$, $-SO_3R_{12}$, $-SO_2NR_{13}R_{14}$ and $-COR_{15}$ in which each of $R_9$ to $R_{15}$ is independently hydrogen, $C_{1-6}$ alkyl, optionally substituted phenyl or optionally substituted phenyl $C_{1-6}$ alkyl;
  or, when m is 2 and m' is 0, two $R_6$'s form a $C_{3-6}$ polymethylene group,
  and $R_7$ is hydrogen or $C_{1-6}$ alkyl, such as methyl or ethyl.

When $R_6$ or $R_6^a$ is heterocyclyl, it is preferably an aromatic or non-aromatic single or fused ring system having from 5 to 12 ring atoms, comprising up to 4 hetero-atoms in the or each ring, selected from oxygen, nitrogen and sulphur.

Preferred halogens are F, Cl and Br.

When two $R_6$'s are linked they preferably form a fused cyclopentyl or cyclohexyl ring.

Preferably Ar is phenyl and $R_6$ or $R_6^a$ is preferably in the meta and/or para position.

Other examples of Ar are naphthyl, benzothienyl, benzofuranyl, 2,3-dihydrobenzofuranyl, 2,3-dihydrobenzothienyl, indolyl, 2,3-dihydrobenzopiranyl and 2,3-dihydrobenzothio piranyl.

Preferably $R_6$ or is bromine, chlorine, $CF_3$, 2-furanyl, 2-pyrryl, 2-thiazolyl, 2-imidazolyl or 2-thienyl, particularly, when Ar is phenyl, in the meta and/or para position.

X is typically oxygen or a direct bond, and n is typically 0 or 1.

A further preferred group R has the formula (IIa)

$$-(CHR_7)_n-X-\underset{R_y}{\overset{Y-R_x}{\bigcirc}}\quad\text{(IIa)}$$

in which the group $-(CHR_7)_n-X-$, which is as defined in formula II, is in the meta- or para- position with respect to $YR_x$ or $R_y$,
  Y is >C=O, >CHOH, >S=O or >$SO_2$;
  each of $R_x$ and $R_y$ is $C_{1-6}$ alkyl, or $R_x$ and $R_y$ are linked together and $R_x$ represents $-(Z)_m-$ where m is 0 or 1 and Z is O, S or $NR_z$ where $R_z$ is hydrogen or $C_{1-6}$ alkyl,
  and $R_y$ represents $-(CH_2)_q-$ where q is an integer of from 1 to 4, preferably 2 or 3.

A preferred sub-group of formula (IIa) is a group of formula (IIb)

$$-CH_2-\underset{(CH_2)_q}{\overset{Y}{\bigcirc}}(Z)_m\quad\text{(IIb)}$$

in which Y, Z, m, q and the position of $-CH_2-$ are as defined in formula (IIa).

Preferably, q is 2 when Z is oxygen and m is 1, and q is 3 when m is 0.

A further preferred sub-group of formula (IIa) is the group of formula (IIc)

$$-CH_2-\underset{R_y}{\overset{Y-R_x}{\bigcirc}}\quad\text{(IIc)}$$

in which Y is >C=O or >CHOH, each of $R_x$ and $R_y$ is $C_{1-6}$ alkyl, preferably methyl, and the position of $-CH_2-$ is as defined in formula (IIa)

A further preferred group R has the formula (IId)

$$-(CHR_7)_n-X-\underset{(CH_2)_q}{\overset{Y}{\text{Het}}}(Z)_m\quad\text{(IId)}$$

where Het is the remainder of a single aromatic heterocyclic ring, containing from 5 to 6 ring atoms and comprising up to 3 heteroatoms in the ring selected from O, S and N;
  and $R_7$, X, Y, Z, m and q are as defined in formula (IIa)

Particular examples of the group R are:

$-CH_2-\underset{Cl}{\overset{Cl}{\bigcirc}}$,  $-CH_2-\bigcirc-CF_3$, $-CH_2-\bigcirc\hspace{-1em}\bigcirc^{=O}$,  $-CH_2-\bigcirc\hspace{-1em}\bigcirc$,

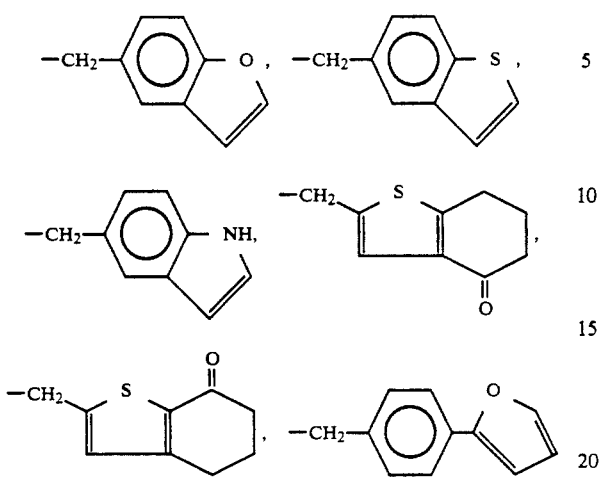

The compounds of formula I or their salts or solvates are preferably in pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

A substantially pure form will generally contain at least 50% (excluding normal pharmaceutical additives), preferably 75%, more preferably 90% and still more preferably 95% of the compound of formula I or its salt or solvate.

One preferred pharmaceutically acceptable form is the crystalline form, including such form in a pharmaceutical composition. In the case of salts and solvates the additional ionic and solvent moieties must also be non-toxic.

Examples of a pharmaceutically acceptable salt of a compound of formula I include the acid addition salts with the conventional pharmaceutical acids, for example, maleic, hydrochloric, hydrobromic, phosphoric, acetic, fumaric, salicylic, citric, lactic, mandelic, tartaric, succinic, benzoic, ascorbic and methanesulphonic.

Examples of a pharmaceutically acceptable solvate of a compound of formula I include the hydrate.

The compounds of formula I have at least one asymmetric centre and therefore exist in more than one stereoisomeric form. The invention extends to all such forms and to mixtures thereof, including racemates.

The present invention also provides a process for the preparation of a compound of formula I which comprises reacting a compound of formula (III):

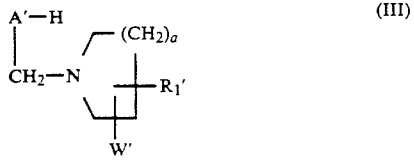

in which a is as defined for formula (I), and A', W$_1$' and R$_1$' are A, W and R$_1$ as defined for formula (I) or a group or atom convertible to A, W and R$_1$, with a compound of formula R' CO.OH or an active derivative thereof, in which R' is R as defined for formula (I), or a group convertible to R, to form a compound of formula (Ia):

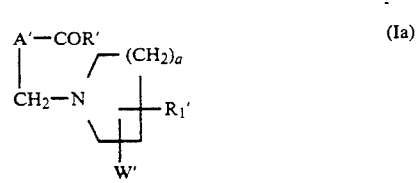

and then optionally performing one or more of the following steps:
a) where A', R', W', or R$_1$' are other than A, R, W and R$_1$, converting A', R', W' or R$_1$' to A, R, W or R$_1$ to obtain a compound of formula (I),
b) where A', R', W' and R$_1$' are A, R, W and R$_1$, converting one A, R, W or R$_1$ to another A, R, W or R$_1$ to obtain a compound of formula (I),
c) forming a salt and/or solvate of the obtained compound of formula (I).

Suitable active derivatives of

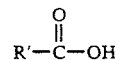

are acid chlorides or acid anhydrides. Another suitable derivative is a mixed anhydride formed between the acid and an alkyl chloroformate.

For example, in standard methods well known to those skilled in the art, the compound of formula (III) may be coupled:
a) with an acid chloride in the presence of an inorganic or organic base,
b) with the acid in the presence of dicyclohexyl carbodiimide, N-dimethylaminopropyl-N,-ethyl carbodiimide or carbonyl diimidazole,
c) with a mixed anhydride generated in situ from the acid and an alkyl (for example ethyl)chloroformate.

It will be appreciated that a compound of formula (Ia) may be converted to a compound of formula (I), or one compound of formula (I) may be converted to another compound of formula (I), by interconversion of suitable substituents. Thus certain compounds of formula (I) and (Ia) are useful intermediates in forming other compounds of the present invention.

For example, compounds of formula (Ia) in which W' is hydroxy and R$_1$' is hydrogen may be converted to compounds in which W and R$_1$ together represent a keto group by oxidation, via a Swern Reaction, using DMSO and oxalyl chloride in dichloromethane and triethylamine.

Also, compounds of formula (I) in which W and R$_1$ together represent a keto group may be converted to other compounds of formula (I) in which W is hydroxyl and R$_1$ is C$_{1-6}$ alkyl by reaction with a C$_{1-6}$ alkyl magnesium halide in an inert solvent, such as diethyl ether or THF.

The above described processes will generally provide a diastereoisomeric mixture which can subsequently separated into isomers by column chromatography.

The compound

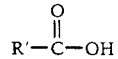

is typically of the formula (IId)

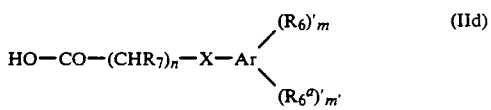

in which $R_6'$ is $R_6$ and $(R_6^a)'$ is $R_6^a$ are as defined for formula (II), or a group or atom convertible to $R_6$ or $R_6^a$, the other variables being as defined for formula (II).

Conversions of substituents $R_6'$ or $(R_6^a)'$ on the aromatic group Ar to obtain $R_6$ or $R_6^a$ are generally known in the art of aromatic chemistry.

$R_6'$ is preferably $R_6$ and $(R_6^a)$, is preferably $R_6^a$.

The compounds of formula I may be converted into their pharmaceutically acceptable acid addition salts by reaction with the appropriate organic or mineral acids.

Solvates of the compounds of formula I may be formed by crystallization or recrystallization from the appropriate solvent. For example hydrates may be formed by crystallization or recrystallization from aqueous solutions, or solutions in organic solvents containing water.

Also salts or solvates of the compounds of formula I which are not pharmaceutically acceptable may be useful as intermediates in the production of pharmaceutically acceptable salts or solvates. Accordingly such salts or solvates also form part of this invention.

As mentioned before, the compounds of formula I exist in more than one stereoisomeric form and the processes of the invention produce mixtures thereof. The individual isomers may be separated one from another by resolution using an optically active acid such as tartaric acid. Alternatively, an asymmetric synthesis would offer a route to the individual form.

Compounds of formula (III) may be prepared from compounds of formula (V) according to the following reaction Scheme I:

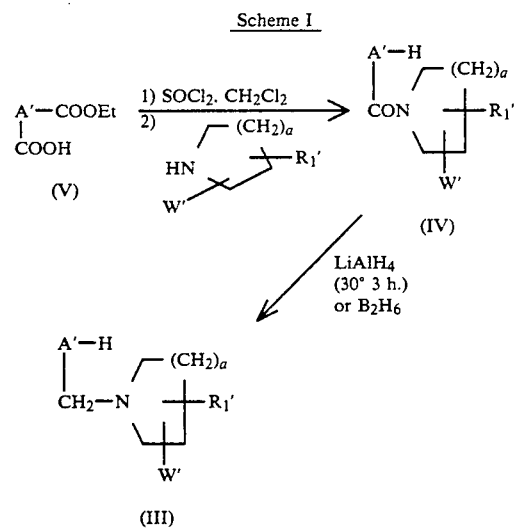

In this scheme, the N-ethoxycarbonyl acid of formula (V) is firstly treated with thionyl chloride and dry methylene chloride, and the reaction mixture is then treated with the appropriate azacyclic compound to produce a cyclic amide intermediate (IV). Reduction of (IV) with $LiAlH_4$ or $B_2H_6$ in an inert nitrogen atmosphere, preferably at about room temperature, yields the compound of formula (III).

Compounds of formula (III) in which A' is

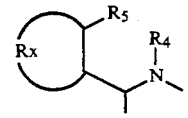

as defined in formula (I), and where $R_4$ and $R_5$ form an optionally substituted $—(CH_2)_c—$ group, may be prepared from compounds of formula (VI) according to the following reaction Scheme 2:

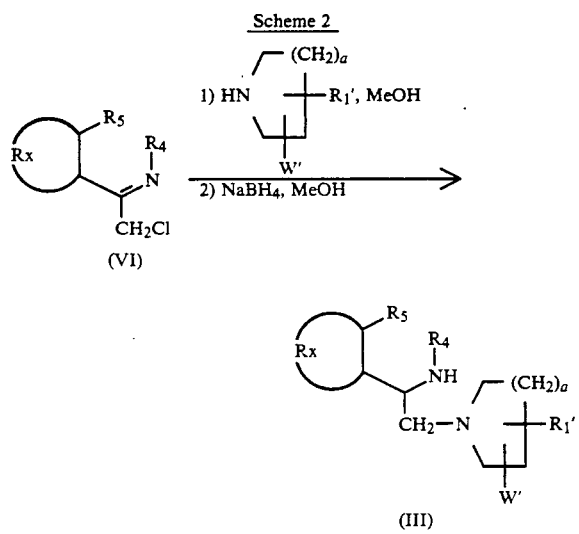

In this scheme, the compound of formula (VI) is firstly treated with the appropriate azacyclic compound in methanol, preferably in an inert nitrogen atmosphere, and the reaction mixture is then treated with sodium borohydride to yield the compound of formula (III).

The conversion of a compound of formula (Ia) to a compound of formula (I) is illustrated by the following reaction Scheme 3:

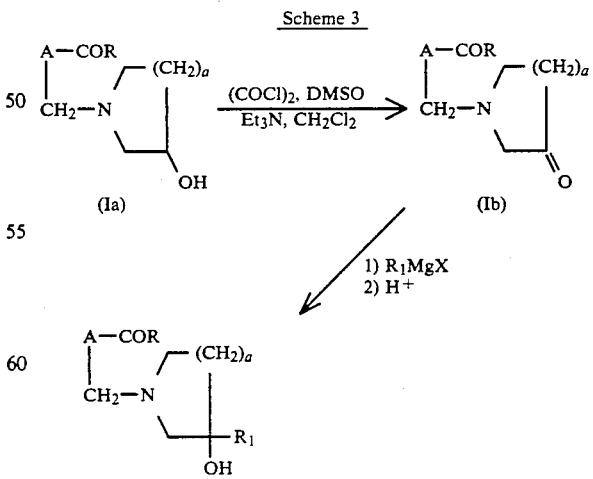

In this scheme, the 3-hydroxypyrrolidin-1-yl derivative of formula (Ia) is converted to the 3-keto compound by oxidation, via a Swern reaction, using DMSO and oxalyl-chloride in dichloromethane and triethylamine at about −60° C. The subsequent conversion to a 3-hydroxy, 3-alkyl derivative is carried out using an alkyl magnesium halide in an inert solvent, such as diethyl ether or THF.

Compounds of formula (V) are novel, and may be prepared by treating the known parent acid with ethyl chloroformate, preferably in the presence of potassium carbonate.

Compounds of formula (VI) are known compounds or can be prepared by known procedures from known compounds, according to, for example, the procedure disclosed in J. Am. Chem. Soc. 59, 2555 (1933).

Compounds of formula R'COOH are also known compounds or can be prepared from known compounds by known methods, for o example, by methods disclosed in EP-A-333315; Zh, Org. Khim. 1975, 11(11), 2400-7; J. Chem. Soc. (B) 1971, (12), 2304-6; J. Med. Chem. 1986, 29,2326-9; C. R. Acad. Sci., Ser. C, 1969, (1) 54-6.

The intermediate compounds of formula (III) described above are novel compounds and as such they form a further aspect of this invention.

The activity of the compounds of formula (I) in standard tests indicates that they are of potential therapeutic utility in the treatment of pain and of hyponatraemic disease states, and of cerebral ischaemia.

Accordingly the present invention also provides a compound of formula (I), or a pharmaceutically acceptable salt or solvate thereof, for use as an active therapeutic substance.

The present invention further provides a pharmaceutical composition comprising a compound of formula (I), or a pharmaceutically acceptable salt or solvate thereof, and a pharmaceutically acceptable carrier.

The present invention also provides the use of a compound of formula (I), or a pharmaceutically acceptable salt or solvate thereof, in the manufacture of a medicament for the treatment of pain, or in the manufacture of a medicament for the treatment of hyponatraemic diseases states, or in the manufacture of a medicament for the treatment of cerebral ischaemia.

Such a medicament, and a composition of this invention, may be prepared by admixture of a compound of the invention with an appropriate carrier. It may contain a diluent, binder, filler, disintegrant, flavouring agent, colouring agent, lubricant or preservative in conventional manner.

These conventional excipients may be employed for example as in the preparation of compositions of known analgesic agents or diuretics or agents for treating cerebral ischaemia.

Preferably, a pharmaceutical composition of the invention is in unit dosage form and in a form adapted for use in the medical or veterinarial fields. For example, such preparations may be in a pack form accompanied by written or printed instructions for use as an agent in the treatment of pain or as a diuretic, or for the treatment of cerebral ischaemia.

The suitable dosage range for the compounds of the invention depends on the compound to be employed and on the condition of the patient. It will also depend, inter alia, upon the relation of potency to absorbability and the frequency and route of administration.

The compound or composition of the invention may be formulated for administration by any route, and is preferably in unit dosage form or in a form that a human patient may administer to himself in a single dosage.

Advantageously, the composition is suitable for oral, rectal, topical, parenteral, intravenous or intramuscular administration. Preparations may be designed to give slow release of the active ingredient.

Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinyl- pyrrolidone, sodium starch glycollate or microcrystalline cellulose; or pharmaceutically acceptable setting agents such as sodium lauryl sulphate.

Solid compositions may be obtained by conventional methods of blending, filling, tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an entericcoating. The composition may also be in the form of an ingestible capsule, for example of gelatin containing the compound, if desired with a carrier or other excipients.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi- dose forms such as a bottle from which the appropriate dose may be withdrawn or a solid form or concentrate which can be used to prepare an injectable formulation.

As mentioned earlier, the effective dose of compound depends s on the particular compound employed, the condition of the patient and on the frequency and route of administration. A unit dose will generally contain from 20 to 1000 mg and preferably will contain from 30 to 500 mg, in particular 50, 100, 150, 200, 250, 300, 350, 400, 450, or 500 mg. The composition may be administered once or more times a day for example 2, 3 or 4 times daily, and the total daily dose for a 70 kg adult will normally be in the range 100 to 3000 mg. Alternatively the unit dose will contain from 2 to 20 mg of active ingredient and be administered in multiples, if desired, to give the preceding daily dose.

Within the above indicated dosage range, no adverse toxicological effects have been observed with compounds of the invention.

The present invention also provides a method for the treatment and/or prophylaxis of pain and/or hyponatraemic disease states and/or cerebral ischaemia in mammals, particularly humans, which comprises administering to the mammal in need of such treatment and/or prophylaxis an effective amount of a compound of formula (I) or a pharmaceutically acceptable salt or solvate thereof.

Compounds of this invention and their preparation are illustrated in the following Examples and summarised in Table (II), the Descriptions illustrating the preparations of intermediates.

Examples Nos. 1,2,3,4,8,10,11,13,15 and 16 are not within the scope of the present invention, and are provided for comparison purposes only.

Description A lethoxycarbonyl pipecolic acid 15.0 g (0.116 moles) of (±) pipecolic acid were dissolved in ml of water.

25.5 g (0.185 moles) of potassium carbonate were added and the solution cooled to +5° C.

19.83 g (0.183 moles) of ethyl chloroformate were added dropwise under mechanical stirring, maintaining the temperature below +10° C.

After 4 hours the reaction mixture was extracted with methylene chloride; the aqueous layer were treated with conc. HCl to acidic pH, extracted with methylene chloride (400 ml) which was dried over Na2SO4 and the solvent evaporated to dryness to afford 23.8 g of the crude product Crystallization from isopropyl ether/n-hexane gave 21.7 g (93% of the theoretical) of the title compound.

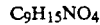

M.W.=201.22
M.P.=82°-84° C.
I.R. (KBr): 3100; 1760; 1650; 1445; 1275; 1195 cm$^{-1}$.
N.M.R. (CDCl$_3$)80 MHz.: δ7.2 (s, 1H); 4.9 (m, 1H); 4.2 (q, 2H); 4.0 (m, 1H); 3.2–2.8 (m, 1H); 2.4–1.1 (m, 6H); 1.2 (t, 3H).

Description 1a 2-(3-hydroxypyrrolidin-1-yl)carbonyl piperidine—diastereoisomeric mixture 2.25 ml (0.031 moles) of thionyl chloride, dissolved in 10 ml of dry methylene chloride, were added dropwise to a stirred solution of 2.25 g (0.011 moles) of N-ethoxycarbonyl pipecolic acid in 40 ml of methylene chloride, cooled below −5° C.

After the addition the reaction mixture was allowed to reach room temperature and the stirring continued 24 h.

The solvent was evaporated in vacuo to dryness and the residue, dissolved in 10 ml of dry methylene chloride, added dropwise to a stirred solution of 1.2 g (0.013 moles) of 3-hydroxypyrrolidine in 40 ml of methylene chloride, cooled below −15° C.

After the addition the reaction mixture was allowed to reach room temperature and the stirring continued overnight.

The organic solution was washed twice with 5% NaHCO$_3$, water, dried over Na$_2$SO$_4$ and the solvent evaporated in vacuo to dryness to yield 2.1 g of the title compound as a brown oil which was sufficiently pure for the following step.

I.R. (neat): 3350; 2930; 1635 cm$^{-1}$.

Description 1b 2-(3-hydroxypyrrolidin-1-yl)methyl piperidine—diastereoisomeric mixture 2.1 g (0.010 moles) of 2-(3-hydroxypyrrolidin-1-yl) carbonyl piperidine, dissolved in 25 ml of dry THF, were added dropwise, under nitrogen atmosphere, to a suspension of 1.0 g (0.025 moles) of lithium aluminium hydride in 50 ml of dry THF, at room temperature After the addition the reaction mixture was allowed to reach room temperature and stirring continued overnight. The alkaline work-up afforded 1.8 g of the title compound as a yellow oil which was sufficiently pure for the following step.

I.R. (neat): 3380; 2935 cm$^{-1}$.

Description 1c 2-(3-fluoropyrrolidin-1-yl)methyl piperidine—diastereoisomeric mixture 3.07 g (16.47 nmoles) of 2-(3-fluoropyrrolidin-1-yl)carboxamido piperidine were dissolved in 50 ml of dry THF.

The solution was warmed to 60° C. and 5.46 ml of a 10M solution of borane dimethylsulfide complex were added dropwise under nitrogen and mechanical stirring.

The reaction mixture was allowed to reflux for 3 hours, cooled to −10° C., carefully treated with 6N HCl and warmed again 3 hours at 70° C.

The solvent was then evaporated in vacuo to dryness and the residue treated with 40% acq. NaOH solution. The crude diamine was exhaustively extracted with diethyl ether, which was dried over Na$_2$SO$_4$ and concentrated in vacuo to dryness.

The residue was purified by flash column chromatography over 230–400 mesh silica gel, eluting with a mixture of CH$_2$Cl$_2$/MeOH/28% NH$_4$OH, 86:10:0.6 respectively, to afford 1.85 g of the title compound.

Description 2

1-(3-hydroxypyrrolidin-1-yl)methyl TM 1,2,3,4-tetrahydroisoquinoline —Diastereoisomeric mixture 2.52 g (0.027 moles) of 3-hydroxypyrrolidine were added to a solution of 0.4 g (0.01 moles) of NaOH in 50 ml of methanol. 2.1 g (0.01 moles) of 1-chloromethyl-3,4-dihydro isoquinoline hydrochloride [J. Am. Chem. Soc. 59, 2555 (1933)]were added portionwise, under nitrogen, to the above stirred solution, cooled below −5° C.

The reaction mixture was stirred for 48 hours at room temperature and then cooled to 0° C; 1.2 g (0.031 moles) of sodium borohydride were added.

After three hours 2 ml of conc. NaOH solution were added and the inorganic salts filtered off. The filtrate was concentrated in vacuo, to afford a residue which was treated with conc. NaOH solution and exhaustively extracted with diethyl ether. The ethereal solution was filtered over celite, dried over $Na_2SO_4$ and the solvent evaporated in vacuo to dryness, to yield 2.2 g of the title compound which was sufficiently pure for the following step.

I.R. (neat): 3400; 2920 cm$^{-1}$.

Description 3

N-benzyl-3-(toluene-4-sulfonyloxy) pyrrolidine 2.39 g (12.4 mmoles) of toluene-4-sulfonyl chloride, dissolved in 10 ml of pyridine, were added dropwise, under nitrogen atmosphere, to a stirred solution of 2.0 g (11.3 mmoles) of N- benzyl-3-hydroxypyrrolidine [J. Med. Pharm. Chem. 1, (1959) 73,76,77]in 15 ml of pyridine, cooled below −10° C.

After the addition, the reaction mixture was kept at 5° C. for 24 h.

The solvent was evaporated in vacuo and the residue washed with 8% $NaHCO_3$, extracted with methylene chloride, dried over $Na_2SO_4$ and the solvent evaporated in vacuo to dryness. The residue was purified by silica gel flash column chromatography eluting with a mixture of hexane/ethyl acetate: 6/4, obtaining 2.0 g of the title compound as a brown oil.

Description 4

N-benzyl-3-fluoro pyrrolidine

A stirred mixture of 1.95 g (5.8 mmoles) of N-benzyl-3-toluene-4-sulfonyloxy)pyrrolidine and 2.0 g (34.4 mmoles) of dry KF in 25 ml of freshly distilled diethylene glycol, was kept at 80° C. for 4 h under nitrogen atmosphere.

The solution was washed with 8% $NaHCO_3$ and exhaustively extracted with diethyl ether.

The organic solution was dried over $Na_2SO_4$ and evaporated in vacuo to dryness.

The residue was purified by silica gel flash column chromatography eluting with a mixture of $CH_2Cl_2/CH_3OH/32\%$ $NH_4OH$: 94/5/0.5, obtaining 0.3 g of the title compound I.R. (neat): 2970; 2780; 1495; 1455 cm$^{-1}$.

N.M.R. (CDCl$_3$) 80 MHz: δ7.5–7.1 (m, 5H); 5.5–5.35 (m, 0.5 H); 4.95–4.65 (m, 0.5 H); 3.65 (s, 2H); 3.05–1.7 (m, 6H).

Description 5

3-fluoro pyrrolidine acetate 0.3 g (1.67 mmoles) of N-benzyl-3-fluoropyrrolidine, dissolved in 20 ml of methanol containing 2.1 ml of acetic acid, were hydrogenated at room temperature in a Parr apparatus at 50 psi in the presence of a catalytic amount of 10% Pd on charcoal, until the theoretical amount of $H_2$ was consumed.

The catalyst was filtered off and the solvent was evaporated in vacuo obtaining 0.18 g of the title compound which was used for the following step as free base.

N.M.R. (CDCl$_3$) 80 MHz: δ10.8–10 3 (s,broad, 2H); 5.7–5.5 (m, 0.5 H); 5.05–4.85 (m, 0.5 H); 3.7–3.0 (m, 4H); 2.5–1.5 (m, 5H).

Description 6

N-benzyl-3-methoxypyrrolidine

A solution of 2.0 g (11 3 mmoles) of N-benzyl-3-hydroxypyrrolidine in 10 ml of dry THF was added dropwise at room temperature to a stirred slurry of 0.53 g (12.4 mmoles) of 56% NaH in 10 ml of dry THF, under nitrogen atmosphere. After 2 h the solution was cooled to 0° C. and 1.8 g (12.4 mmoles) of methyl iodide were added.

The solution was allowed to reach room temperature; the stirring continued for 1 h and then washed with water. The organic layer was dried over $Na_2SO_4$ and evaporated in vacuo to dryness.

The residue was purified y silica gel flash column chromatography, eluting with a mixture of $CH_2Cl_2/CH_3OH/32\%NH_4OH$ : 94/5/0.5, obtaining 0.9 g of the title compound.

I.R. (neat): 2940; 2780; 1495; 1455 cm$^{-1}$.

N.M.R. (CDCl$_3$) 80 MHz: δ7.35–7.1 (m, 5H); 4.05–3.7 (m, 1H); 3.55 (s, 2H); 3.2 (s, 3H); 2.95–2.2 (m, 4H); 2.2–1.6 (m, 2H).

Description 7

3-methoxypyrrolidine hydrochloride 0.9 g (4.7 mmoles) of N-benzyl-3-methoxypyrrolidine, dissolved in 20 ml of methanol containing 1.2 ml of acetic acid, were hydrogenated at room temperature in a Parr apparatus at 50 psi in the presence of a catalytic amount of 10% Pd on charcoal, until the theoretical amount of $H_2$ was consumed.

The catalyst was filtered off and the solvent was evaporated in vacuo. The residue was taken up in 5 ml of 40% NaOH, exhaustively extracted with diethyl ether and dried over $Na_2SO_4$ The solution was brought to acidic pH with HCl/diethyl ether and the solvent evaporated in vacuo to dryness obtaining 0.45 g of the title compound which was used for the following step as free base.

N.M.R. (CDCl$_3$) 80 MHz: δ10.3–9.1 (s,broad, 2H); 4.1–3.9 (m, 1H); 3.9–3 1 (m, 7H); 2.3–1.8 (m, 2H).

Description 8

(3R)-N-benzyloxycarbonyl-3-(toluene-4-sulfonyloxy)-pyrrolidine 22.25 g (0.117 moles) of toluene-4-sulfonyl chloride, dissolved in 30 ml of pyridine, were added dropwise to a stirred solution of 11.79 g (0.053 moles) of (3R)-N-benzyloxycarbonyl-3-hydroxypyrrolidine [J. Chem. Soc., Chem. Commun. 1984, 1298]in 50 ml of pyridine, cooled below 0° C. After the addition, the reaction mixture was kept at 5° C. for 48 hours.

The solvent was evaporated in vacuo to dryness; the residue, dissolved in 500 ml of methylene chloride, was washed with 10% citric acid, water and 8% $NaHCO_3$, dried over $Na_2SO_4$ and evaporated in vacuo to dryness.

The crude product was purified by silica gel flash column chromatography, eluting with a mixture of n-hexane/AcOEt 7:3, to yield 18.07 g (90% of the theoretical) of the title compound.

$C_{19}H_{21}NO_5S$

M.W.=375.430

I.R. (neat): 2960; 2880; 1710; 1600; 1420; 1360; 1170 cm$^{-1}$.

$[\alpha]_D^{20} = -4.55$ (C=3, MeOH).

Description 9

(3S)-N-benzyloxycarbonyl-3-fluoropyrrolidine

A stirred mixture of 20.85 g (0.360 moles) of potassium fluoride spray-dried and 18.0 g (0.048 moles) of (3R)-N-benzyloxycarbonyl-3-hydroxypyrrolidine in 160 ml of freshly distilled ethylene glycol was kept at 85° C. for 15 h under nitrogen atmosphere.

The reaction mixture was diluted with 5 parts of water and exhaustively extracted with ethyl acetate. The organic solution was washed with a saturated solution of NaCl/H$_2$O, dried over Na$_2$SO$_4$ and evaporated in vacuo to dryness.

The residue was purified by silica gel flash column chromatography, eluting with a mixture of n-hexane/AcOEt 6:4 to yield 7.03 g (66% of the theoretical) of the title compound.

C$_{12}$H$_{14}$FNO$_2$

M.W. = 223.240

I.R. (neat): 2970; 2890; 1705; 1420; 1350 cm$^{-1}$.

N.M.R. (CDCl$_3$) 80 MHz: δ7.35 (s, 5H); 5.23 (dm, J$_{HF}$=53 Hz, 1H); 5.15 (s, 2H); 3.10-3.80 (m, 4H); 1.50-2.35 (m, 2H).

$[\alpha]_D^{20} = +22.36$ (C=3, MeOH).

Description 10

(3S)-3-fluoropyrrolidine hydrochloride 6.50 g (0.029 moles) of (3S)-N-benzyloxycarbonyl-3-fluoropyrrolidine, dissolved in 150 ml of 90% acetic acid, were hydrogenated in a Parr apparatus in the presence of 800 mg of. 10% Palladium on charcoal at 45 psi for 5 h.

The catalyst was filtered off and the filtrate evaporated in vacuo to dryness.

The residue was taken up in 40% NaOH and exhaustively extracted with diethyl ether.

The organic solution was dried over Na$_2$SO$_4$ and treated with HCl/Et$_2$O. The solvent was evaporated in vacuo to dryness to yield 3.51 g (96% of the theoretical) of the title compound.

C$_4$H$_8$FN.HCl

M.W. = 125.577
M.P. = 135°-136° C.

N.M.R. (CDCl$_3$) 300 MHz as free base: δ5.20 (dt, J$_{HF}$=55 Hz, 1H); 3.10-3.30 (m, 2H); 2.70-2.90 (m, 2H); 1.78-2.08 (m, 2H); 1.95 (s, 1H).

$[\alpha]_D^{20} = +8.27$ (C=3, MeOH).

Description 11

(3R)-3-fluoropyrrolidine hydrochloride

The title compound was prepared starting from (3S)-N-benzylqxycarbonyl-3-hydroxypyrrolidine [Synthetic Commun. 1986, 16, 1815] and following descriptions 8, 9 and 10. This compound was identical to the (3S)-3-fluoropyrrolidine hydrochloride (description 10) in all except for the sign of its optical rotation.

Table 1 summarises structures and synthetic methods for intermediate diamines.

TABLE I

| (A)— | n | W | *• | MOLECULAR FORMULA | MOLECULAR WEIGHT | SYNTHETIC DESCRIPTION |
|---|---|---|---|---|---|---|
|  | 1 | OH | DIAST. MIX. | C$_{10}$H$_{20}$N$_2$O | 184.276 | 1a, 1b (i) |
| | 1 | OH | S*, S* | C$_{10}$H$_{20}$N$_2$O | 184.276 | 1a, 1b (ii) |
| | 1 | OH | S*, R* | C$_{10}$H$_{20}$N$_2$O | 184.276 | 1a, 1b (ii) |
| | 1 | OH | DIAST. MIX. | C$_{12}$H$_{24}$N$_2$O | 212.328 | 1a, 1b (i) |

TABLE I-continued $$\underset{CH_2N}{\overset{(A)-H}{\big|}}\underset{W}{\overset{(CH_2)_n}{\diagdown}}$$

| (A)— | n | W | *● | MOLECULAR FORMULA | MOLECULAR WEIGHT | SYNTHETIC DESCRIPTION |
|---|---|---|---|---|---|---|
| 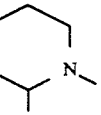 | 1 | OH | DIAST. MIX. | $C_{12}H_{24}N_2O$ | 212.328 | 1a, 1b (i) |
| 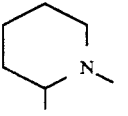 | 2 | OH | DIAST. MIX. | $C_{11}H_{22}N_2O$ | 198.302 | 1a, 1b |
| 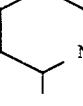 | 1 | OH | DIAST. MIX. | $C_{14}H_{20}N_2O$ | 232.316 | 2 (i) |
| 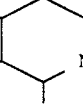 | 1 | OH | DIAST. MIX. | $C_{16}H_{24}N_2O$ | 260.368 | 2 (i) |
| 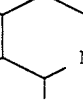 | 2 | OH | DIAST. MIX. | $C_{15}H_{22}N_2O$ | 246.342 | 2 |
| 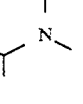 | 1 | F | DIAST. MIX. | $C_{10}H_{19}FN_2$ | 186.268 | 1a, 1c (iii) |
| 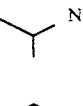 | 1 | F | DIAST. MIX. | $C_{12}H_{23}FN_2$ | 214.320 | 1a, 1c (iii) |
| 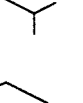 | 1 | F | DIAST. MIX. | $C_{12}H_{23}FN_2$ | 214.320 | 1a, 1c (iii) |
| 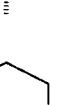 | 1 | F | S*, S● | $C_{10}H_{19}FN_2$ | 186.268 | 1a, 1c (iv) |
|  | 1 | F | S*, R● | $C_{10}H_{19}FN_2$ | 186.268 | 1a, 1c (v) |

TABLE I-continued

| (A)— | n | W | *● | MOLECULAR FORMULA | MOLECULAR WEIGHT | SYNTHETIC DESCRIPTION |
|---|---|---|---|---|---|---|
| piperidinyl | 1 | OCH₃ | DIAST. MIX. | $C_{11}H_{22}N_2O$ | 198.302 | 1a, 1b (vi) |

(i) (±)-3-hydroxy pyrrolidine was prepared as described in: J. Med. Pharm. Chem. 1 (1959) 73, 76, 77; Doklady Akad. S.S.S.R. 117 (1957) 813, 815; Pr. Acad. Sci. U.S.S.R. Chem. Sect. 112–117 (1957) 1059.
(ii) Enantiomeric pure 3-hydroxy pyrrolidines were prepared as described in: Synthetic Communication 15(7), 587–598 (1985).
(iii) (±)-3-fluoropyrrolidine was prepared following descriptions n° 3, 4, 5.
(iv) (3S)-3-fluoropyrrolidine was prepared following descriptions n° 8, 9, 10.
(v) (3R)-3-fluoropyrrolidine was prepared following description 11.
(vi) (±)-3-methoxypyrrolidine was prepared following descriptions n° 6, 7.

EXAMPLE 1

1-(3,4-dichlorophenyl)acetyl-2-(3-hydroxypyrrolidin-1-yl)methyl piperidine hydrochloride—Diasrereoisomeric mixture 1.33 g (6.0 mmoles) of 3,4-dichlorophenylacetyl chloride, dissolved in 20 ml of dry chloroform, were added dropwise at −10° C. to a stirred solution of 1.0 g (5.42 mmoles) of 2-(3-hydroxypyrrolidin-1-yl) methyl piperidine—diast. mix.—dissolved in 20 ml of dry chloroform in the presence of 0.82 g (6.0 mmoles) of anhydrous potassium carbonate. The reaction mixture was allowed to reach room temperature and stirred overnight, washed with water, 5% NaOH solution and dried over $Na_2SO_4$; the solvent was evaporated in vacuo to dryness to afford 2.1 g of the crude product which was purified by silica gel column chromatography eluting with methylene chloride containing increasing amounts of methanol (0.1–1%). The purified free base was dissolved in 20 ml of acetone and the solution brought to acidic pH with HCl/diethyl ether. The precipitate was filtered, washed and dried, to yield 1.0 g of the title compound.

$C_{18}H_{24}Cl_2N_2O_2$. HCl

M.P.=218°–219° C.
M.W.=407.767
Elemental analysis: calcd. C,53.01; H,6.18; N,6.87; Cl,26.09; found C,53.05; H,6.26; N,6.74; Cl,25.84.
I.R. KBr: 3300; 2950; 1640; 1440 cm⁻¹.
N.M.R. (CDCl₃) (80 MHz) Free base.: δ7.0–7.5 (m, 3H); 3.3–5.2 (m, 5H); 2.0–3.2 (m, 9H); 1.1–2.0 (m, 7H).

EXAMPLE 2

1-(4-trifluoromethylphenyl)acetyl-2-(3-hydroxypyrrolidin-1-yl)methyl piperidine hydrochloride—Diastereoisomeric mixture Prepared as Example n° 1 from 0.95 g (5.1 mmoles) of 2-(3-hydroxypyrrolidin-1-yl)methyl piperidine—diast. mix.—,1.25 g (5.6 mmoles) of 4-trifluoromethylphenylacetyl chloride and 0.77 g (5.6 mmoles) of anhydrous potassium carbonate.

The work-up afforded 1.9 g of the crude product which was purified by silica gel column chromatography as described in Ex. 1.

The purified free base was dissolved in 20 ml of acetone and the solution brought to acidic pH with HCl/diethyl ether. The precipitate was filtered, washed and dried, to yield 0.8 g of the title compound.

$C_{19}H_{25}F_3N_2O_2$. HCl

M.P.=135°–137° C.
M.W.=406.871
Elemental analysis: calcd. C,56.08; H,6.44; N,6.88; Cl,8.71; found C,55.66; H,6.49; N,6.80; Cl,8.74.
N.M.R. (CDCl₃) (80 MHz): δ10.9–11.5 (s broad, 1H); 7.3–7.7 (m, 4H); 5.1–5.3 (m, 1H); 2.5–4.7 (m, 12H); 1.8–2.5 (m, 2H); 1.3–1.8 (m, 6H).

EXAMPLE 3

(2S)-1-(3,4-dichlorophenyl)acetyl-2-[(3S)-hydroxypyrrolidin-1-yl]methyl piperidine hydrochloride Prepared as Example n° 1 from 2.0 g (10.8 mmoles) of (2S)-[(3S)-hydroxypyrrolidin1-yl]methyl piperidine, 2.64 g (11.8 mmoles) of 3,4-dichlorophenylacetyl chloride and 1.58 g (11.8 mmoles) of anhydrous potassium carbonate.

The work-up afforded 3.6 g of the crude product which was purified by silica gel chromatography as described in Ex. 1.

The purified free base was dissolved in 40 ml of acetone and the solution brought to acidic pH with HCl/diethyl ether. The precipitate was filtered, washed and dried, to yield 1.5 g of the title compound.

$C_{18}H_{24}Cl_2N_2O_2$. HCl

M.P.=199°–200° C. M.W.=407.767
Elemental analysis: calcd. C,53.01; H,6.18; N,6.87; Cl,26.09; found C,52.88; H,6.20; N,6.79; Cl,26.11.
I.R. (KBr): 3300; 2950; 1640; 1440 cm⁻¹.
N.M.R. (CDCl₃) (80 MHz) free base: δ7.0–7.5 (m, 3H); 3.3–5.2 (m, 5H); 2.0–3.2 (m, 9H); 1.1–2.0 (m, 7H).
$[\alpha]_D^{20}$=−43.0 (C=1, MeOH).

EXAMPLE 4

(2S)-1-(3,4-dichlorophenyl)acetyl-2-[(3R)-hydroxypyrrolidin-1-yl]methyl piperidine hydrochloride monohydrate Prepared as Example n° 1 from 1.8 g (9.7 mmoles) of (2S)-[(3R)-hydroxypyrrolidin-1-yl]methyl piperidine, 2.3 g (10.6 mmoles) of 3,4-dichlorophenylacetyl chloride and 1.46 g (10.6 mmoles) of anhydrous potassium carbonate.

The work-up afforded 3.2 g of the crude product which was purified by silica gel chromatography as described in Ex. 1.

The purified free base was dissolved in 40 ml of acetone and the solution brought to cidic pH with HCl/diethyl ether. The precipitate was filtered, washed and dried, to yield 0.9 g of the title compound.

$C_{18}H_{24}Cl_2N_2O_2 \cdot HCl \cdot H_2O$

M.P.=92°–94° C.
M.W.=425.783
Elemental analysis: calcd. C,50.77; H,6.39; N,6.58; Cl,24.98; found C,50.74; H,6.33; N,6.61; Cl,25.09.
I.R. (KBr) : 3300; 2950; 1640; 1440 cm$^{-1}$.
N.M.R. (CDCl$_3$) (80 MHz) Free base: δ7.0–7.5 (m, 3H); 3.3–5.2 (m, 5H); 2.0–3.2 (m, 9H); 1.1–2.0 (m, 7H).
$[\alpha]_D^{20} = -48.0$ (C=1, MeOH).

EXAMPLE 5

1-(4-trifluoromethylphenyl)acetyl-2-(3-hydroxypyrrolidin-1-yl) methyl-3,3-dimethyl piperidine hydrochloride—Diastereoisomeric mixture Prepared as Example n° 1 from 1.0 g (4.7 mmoles) of 2-(3-hydroxypyrrolidin-1-yl)methyl-3,3-dimethyl piperidine—diast. mix.—, 1.1 g (5.1 mmoles) of 4-trifluoromethylphenylacetyl chloride and 0.7 g (5.1 mmoles) of anhydrous potassium carbonate.

The workup afforded 1.8 g of the crude product which was purified by silica gel chromatography as described in Ex. 1.

The purified free base was dissolved in 20 ml of acetone and the solution brought to acidic pH with HCl/diethyl ether. The precipitate was filtered, washed and dried, to yield 0.4 g of the title compound.

$C_{21}H_{29}F_3N_2O_2 \cdot HCl$

M.P.=238°–241° C.
M.W.=434.923
Elemental analysis: calcd. C, 57.99; H, 6.95; N, 6.44; Cl, 8.15; F, 13.11; found C, 57.98; H, 6.98; N, 6.43; Cl, 8.20; F, 12.98.
I.R. (KBr): 3300; 2960; 2700; 1630; 1425; 1340 cm$^{-1}$.

EXAMPLE 6

1-(3,4-dichlorophenyl)acetyl-2-(3-hydroxypyrrolidin-1-yl)methyl -3,3-dimethyl piperidine hydrochloride—Diastereoisomeric mixture Prepared as Example n° 1 from 1.0 g (4.7 mmoles) of 2-(3-hydroxypyrrolidin-1-yl)methyl-3,3-dimethyl piperidine—diast. mix.—, 1.1 g (5.1 mmoles) of 3,4-dichlorophenylacetyl chloride and 0.7 g (5.1 mmoles) of anhydrous potassium carbonate.

The work-up afforded 1.7 g of the crude product which was purified by silica gel chromatography as described in Ex. 1.

The purified free base was dissolved in 20 ml of acetone and the solution brought to acidic pH with HCl/diethyl ether. The precipitate was filtered, washed and dried, to yield 0.4 g of the title compound.

$C_{20}H_{28}Cl_2N_2O_2 \cdot HCl$

M.P.=215°–218° C.

M.W.=435.819
Elemental analysis: calcd. C,55.11; H, 6.71; N,6.43; Cl,24.41; found C,55.12; H, 6.74; N,6.42; Cl,24.39.
I.R. (KBr) : 3295; 2950; 2695; 1630; 1470 cm$^{-1}$.

EXAMPLE 7

1-(3,4-dichlorophenyl)acetyl-2-(3-hydroxypyrrolidin-1-yl)methyl -4,4-dimethyl piperidine hydrochloride hemihydrate—Diastereoisomeric mixture Prepared as Example n° 1 from 0.6 g (2.8 mmoles) of 2-(3-hydroxypyrrolidin-1-yl)methyl-4,4-dimethyl piperidine—diast. mix.—, 0.7 g (3.1 mmoles) of 3,4-dichlorophenylacetyl chloride and 0.4 g (3.1 mmoles) of anhydrous potassium carbonate.

The work-up afforded 0.9 g of the crude product which was purified by silica gel chromatography as described in Ex. 1.

The purified free base was dissolved in 20 ml of a mixture of acetone and ethyl acetate 1:1. The solution was brought to acidic pH with HCl/diethyl ether. The precipitate was filtered, washed and dried, to yield 0.2 g of the title compound.

$C_{20}H_{28}Cl_2N_2O_2 \cdot HCl \cdot \frac{1}{2}H_2O$

M.P.=163°–166° C.
M.W.=444.827
Elemental analysis: calcd. C,53.99; H, 6.79; N,6.29; Cl,23.91; found C,53.80; H, 6.66; N,6.27; Cl,23.94.
I.R. (KBr) : 3300; 2950; 1635; 1440 cm$^{-1}$.

EXAMPLE 8

(R,S)-1-(3,4-dichlorophenyl)acetyl-2-(3-oxopyrrolidin-1-yl)methyl piperidine hydrochloride 1.37 ml (19.0 mmoles) of dimethyl sulfoxyde were added dropwise, at $-60°$ C., under nitrogen atmosphere, to a stirred solution of 0.76 ml (8.8 mmoles) of oxalyl chloride in 15 ml of dry methylene chloride.

After 5 minutes a solution of 3.0 g (8.0 mmoles) of 1-(3,4-dichlorophenyl)acetyl-2-(3-hydroxypyrrolidin-1-yl)methyl piperidine (diastereoisomeric mixture) in 20 ml of dry methylene chloride, was added dropwise to the above solution kept at $-60°$ C. for 15 minutes.

5.5 ml (40 mmoles) of triethylamine were then added dropwise and the reaction mixture allowed to reach room temperature, stirred 1 hour, washed with water, extracted with methylene chloride and dried over Na$_2$SO$_4$. The solvent was evaporated in vacuo to dryness to afford 3.0 g of the crude product which was purified by silica gel chromatography eluting with methylene chloride containing increasing amounts of methanol (0.1–1%).

The purified free base was dissolved in 50 ml of acetone and the solution brought to acidic pH with HCl/diethyl ether. The precipitate was filtered, washed and dried, to yield 2.3 g of the title compound.

$C_{18}H_{22}Cl_2N_2O_2 \cdot HCl$

M.P.=213°14 214° C.
M.W.=405.751
Elemental analysis: calcd. C,53.28; H, 5.71; N,6.90; Cl,26.21; found C,53.48; H, 5.86; N,6.54; Cl,25.62.
I.R. (neat) fee base: 2940; 1725; 1640; 1470 cm$^{-1}$

EXAMPLE 9

(R,S)-1-(3,4-dichlorophenyl)acetyl-2-(3-hydroxy-3-methylpyrrolidin-1-yl) methyl piperidine hydrochloride-Diastereoisomer A A solution of 0.9 g (2.4 mmoles) of (R,S)-1-(3,4-dichlorophenyl)acetyl-2-(3-oxopyrrolidin-1-yl)methyl piperidine in 10 ml of dry diethyl ether was added dropwise, at room temperature, to a stirred solution of CH3MgBr, obtained from 0.38 g (15.6 mmoles) of Mg and 0.93 ml (15.6 mmoles) of CH3I in 40 ml of dry diethyl ether.

The reaction mixture was stirred for 2 hours and then treated with a saturated solution of NH4Cl, extracted twice with diethyl ether, dried and evaporated in vacuo to dryness. The residue was purified by silica gel chromatography eluting with methylene chloride containing increasing amounts of methanol (0.1–2%). The purified free base was dissolved in 10 ml of ethyl acetate and the solution brought to acidic pH with HCl/diethyl ether. The precipitate was filtered, washed and dried, to yield 0.18 g of the title compound.

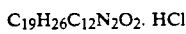

$C_{19}H_{26}Cl_2N_2O_2$. HCl

M.P.=174°–176° C.
M.W.=421.793
Elemental analysis: calcd. C,54.10; H, 6.45; N,6.64; Cl,25.22; found C,54.09; H, 6.49; N,6.56; Cl,25.01.

EXAMPLE 10

1-(3,4-dichlorophenyl)acetyl-2-(3-hydroxypiperidin-1-yl) methyl piperidine hydrochloride diastereoisomeric mixture Prepared as Example n° 1 from 3.2 g (16.0 mmoles) of 2-(3-hydroxypiperidin-1-yl)methyl piperidine—diast. mix.—, 3.9 g (17.5 mmoles) of 3,4-dichlorophenylacetyl chloride and 2.5 g (17.5 mmoles) of anhydrous potassium carbonate.

The work-up afforded 5.5 g of the crude product which was purified by silica gel chromatography as described in Ex. 1.

The purified free base was dissolved in 80 ml of acetone and the solution was brought to acidic pH with HCl/diethyl ether. The precipitate was filtered, washed and dried, to yield 3.0 g of the title compound.

$C_{19}H_{26}Cl_2N_2O_2$. HCl

M.P.=205°–207° C.
M.W.=421.793
Elemental analysis: calcd. C,54.10; H, 6.45; N,6.64; Cl,25.22; found C,53.80; H, 6.46; N,6.56; Cl,25.03.
I.R. (neat) free base : 3400; 2920; 1640; 1440 cm$^{-1}$
N.M.R. CDCl3) (80 MHz): δ10.6–11.2 (s broad, 1H); 7.1–7.5 (m, 3H); 5.1–5.55 (m, 1H ; 3.2–4.4 (m, 6H); 2.2–3.2 (m, 6H); 1.0–2.2 (m, 10H).

EXAMPLE 11

(R,S)-1-(3,4-dichlorophenyl)acetyl-2-(3-oxopiperidin-1-yl) methyl piperidine hydrochloride Prepared as Example n° 8 from 0.66 ml (7.6 mmoles) of oxalyl chloride, 1.1 ml (15.2 mmoles) of dimethyl sulfoxyde, 2.67 g (7.0 mmoles) of 1-(3,4-dichlorophenyl)acetyl-2-(3-hydroxypiperidin-1-yl)methyl piperidine—diast. mix.—and 4.8 ml (35 mmoles) of triethylamine.

The work-up afforded 2.7 g of the crude product which was purified by silica gel chromatography as described in Ex. 8. The purified free base was dissolved in 50 ml of acetone and the solution brought to acidic pH with HCl/diethyl ether. The precipitate was filtered, washed and dried, to yield 1.7 g of the title compound.

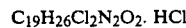

$C_{19}H_{24}Cl_2N_2O_2$. HCl

M.P.=214°–216° C.
M.W.=419.777
Elemental analysis: calcd. C,54.36; H, 6.00; N,6.67; Cl,25.35; found C,53.73; H, 6.11; N,6.49; Cl,24.98.
I.R. (neat) free base: 2940; 2860; 1725; 1630; 1470 cm$^{-1}$.
N.M.R. (CDCl3) (80 MHz) Free base: δ7.0–7.5 (m, 3H); 4.8–5.3 (m, 1H); 3.7 (s, 2H); 3.2–3.7 (m, 1H); 3.0 (s, 2H); 2.1–3.0 (m, 7H); 1.1–2.1 (m, 8H).

EXAMPLE 12

1-(3,4-dichlorophenyl)acetyl-2-(3-hydroxy-3-methyl piperidin-1-yl) methyl piperidine—Diastereoisomeric mixture Prepared as Example n° 9 from 1.2 g (3.1 mmoles) of (R,S)-1-(3,4-dichlorophenyl)acetyl-2-(3-oxopiperidin-1-yl)methyl piperidine, 0.38 g (15.6 mmoles) of Mg and 0.93 ml (15.6 mmoles) of CH3I.

The work-up afforded 1.0 g of the crude product which was purified by silica gel chromatography, eluting with methylene chloride containing increasing amounts of methanol (0.1–2%), to yield 0.5 g of the title compound as a yellow oil.

$C_{20}H_{28}Cl_2N_2O_2$

M.W.=399.354
N.M.R. (CDCl3) (80 Mhz) Free base: δ6.9–7.5 (m, 3H); 4.5–5.2 (m, 1H); 3.4–3.9 (m, 3H); 2.2–3.4 (m, 6H); 1.3–2.2 (m, 12H), 1.2 (s, 3H).

EXAMPLE 13

1-(3-hydroxypyrrolidin-1-yl)methyl-2-(3,4-dichlorophenyl)acetyl -1,2,3,4-tetrahydroisoquinoline hydrochloride—diastereoisomeric mixture Prepared as Example n° 1 from 5.0 g (21.5 mmoles) of 1-(3-hydroxypyrrolidin-1-yl)methyl-1,2,3,4-tetrahydroisoquinoline—diast. mix.—, 5.2 g (23.6 mmoles) of 3,4-dichlorophenylacetyl chloride and 3.6 g (23.6 mmoles) of anhydrous potassium carbonate.

The work-up afforded 8.5 g of the crude product which was purified by silica gel chromatography as described in Ex. 1. The purified free base was dissolved in 50 ml of acetone and the solution brought to acidic pH with HCl/diethyl ether. The precipitate was filtered, washed and dried, to yield 3.0 g of the title compound.

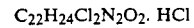

$C_{22}H_{24}Cl_2N_2O_2$. HCl

M.P.=215°–217° C.
M.W.=455.807
Elemental analysis: calcd. C,57.97; H, 5.53; N,6.15; Cl,23.34; found C,57.91; H, 5.53; N,6.20; Cl,23.06.

EXAMPLE 14

1-(3-hydroxypyrrolidin-1-yl)methyl-2-(3,4-dichlorophenyl)acetyl 4,4-dimethyl-1,2,3,4-tetrahydroisoquinoline hydrochloride—diastereoisomeric mixture Prepared as Example n° 1 from 2.4 g (9.2 mmoles) of 1-(3-hydroxypyrrolidin-1-yl)methyl-4,4-dimethyl-1,2,3,4-tetrahydroisoquinoline —diast. mix.—, 2.3 g (10.3 mmoles) of 3,4-dichlorophenylacetyl chloride and 1.4 g (10.3 mmoles) of anhydrous potassium carbonate.

The work-up afforded 4.0 g of the crude product which was purified by silica gel chromatography as described in Ex. 1.

The purified free base was dissolved in 30 ml of acetone and the solution brought to acidic pH with HCl/diethyl ether. The precipitate was filtered, washed and dried, to yield 2.0 g of the title compound.

$C_{24}H_{28}Cl_2N_2O_2 \cdot HCl$

M.P.=284°-286° C.
M.W.=483.3.859
Elemental analysis: calcd. C,59.57; H, 6.04; N,5.79; Cl,21.98; found C,59.52; H, 6.08; N,5.41; Cl,20.57.

EXAMPLE 15

(R,S)-1-(3-hydroxypiperidin-1-yl)methyl-2-(3,4-dichlorophenyl) acetyl-1,2,3,4-tetrahydroisoquinoline hydrochloride—diastereoisomer A Prepared as Example n° 1 from 4.83 g (19.6 mmoles) of 1-(3-hydroxypiperidin-1-yl)methyl-1,2,3,4-tetrahydroisoquinoline—diast. mix.—, 5.15 g (23.1 mmoles) of 3,4-dichlorophenylacetyl chloride and 3.2 g (23.1 mmoles) of anhydrous potassium carbonate.

The work-up afforded 9.0 g of the crude product which was purified by silica gel chromatography eluting with methylene chloride containing increasing amounts of methanol (0.1–1%). The least polar product was dissolved in acetone and the solution brought to acidic pH with HCl/diethyl ether. The precipitate was filtered, washed and dried, to yield 0.4 g of the title compound.

$C_{23}H_{26}Cl_2N_2O_2 \cdot HCl$

M.P.=210°-214° C.
M.W.=469.833
Elemental analysis: calcd. C,58.79; H, 5.79; N,5.96; Cl,22.64; found C,57.98; H, 5.87; N,5.64; Cl,21.32.

EXAMPLE 16

(R,S)-1-(3-hydroxypiperidin-1-yl)methyl-2-(3,4-dichlorophenyl) acetyl-1,2,3,4-tetrahydroisoquinoline hydrochloride—diastereoisomer B Continuing the elution of the chromatographic column of Example n° 15 a second product was obtained and crystallized as its picrate salt.

Elemental analysis: calcd. C,52.57; H,4.41; N,10.57; Cl,10.70; found C,52.62; H,4.43; N,10.59; Cl,10.77.

The corresponding free base, dissolved in 20 ml of acetone, was treated with HCl/diethyl ether. The precipitate was filtered, washed and dried, to yield 0.45 g of the title compound.

$C_{23}H_{26}Cl_2N_2O_2 \cdot HCl$

M.P.=222°-224° C.
M.W.=469.833
Elemental analysis: calcd. C,58.79; H, 5.79; N,5.96; Cl,22.64; found C,57.98; H, 5.70; N,5.88; Cl,22.41.

EXAMPLE 17

1-[1-oxo-3,4-dihydro-(2H)-napht-6-yl]acetyl-2-(3-hydroxy-pyrrolidin-1-yl)methyl piperidine—diastereoisomeric mixture Prepared as Example n° 1 from 1.05 g (5.7 mmoles) of 2-(3-hydroxypyrrolidin-1-yl)methyl piperidine—diast. mix.—, 1.4 g (6.2 mmoles) of [1-oxo-3,4-dihydro-(2H)-napht-6-yl]acetyl chloride and 0.86 g (6.2 mmoles) of anhydrous potassium carbonate.

The work-up afforded 2.1 g of the crude product which was purified by silica gel chromatography as described in Ex. 1.

The purified free base was dissolved in 20 ml of acetone and the solution brought to acidic pH with HCl/diethyl ether. The precipitate was filtered, washed and dried, to yield 0.6 g of the title compound.

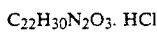

$C_{22}H_{30}N_2O_3 \cdot HCl$

M.P.=192°-193° C.
M.W.=406.941
Elemental analysis: calcd. C,64.93; H, 7.68; N,6.88; Cl,8.71; found C,64.34; H, 7.64; N,6.73; Cl,8.47.

N.M.R. (CDCl₃) (80 MHz): δ10.4–10.8 (s broad, 1H); 7.9–8.1 (m, 1H); 7.0–7.3 (m, 2H); 5.0–5.4 (m, 1H); 4.3–4.7 (m, 1H); 1.0–4.3 (m, 25H).

EXAMPLE 18

1-(3,4-dichlorophenyl)acetyl-2-(3-fluoropyrrolidin-1-yl)methyl piperidine hydrochloride diastereoisomeric mixture Prepared as Example No. 1 from 0.98 g (5.3 mmoles) of 2-(3-fluoropyrrolidin-1-yl)methyl piperidine—diast. mix.—, 1.3 g (5.83 mmoles) of 3,4-dichlorophenylacetyl chloride and 0.8 g (5.83 mmoles) of anhydrous potassium carbonate.

The work-up afforded 1.5 g of the crude product which was purified by silica gel column chromatography as described in Ex. 1.

The purified free base was dissolved in 30 ml of acetone and the solution brought to acidic pH with HCl/diethyl ether. The precipitate was filtered, washed and dried, to yield 0.9 g of the title compound.

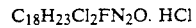

$C_{18}H_{23}Cl_2FN_2O \cdot HCl$

M.P.=237°-240° C.
M.W=409.759
Elemental analysis: Calcd. C,52.75; H,5.90; N,6.83; Cl,25.96; F, 4.63; Found C,52.21; H,5.84; N,6.65; Cl,25.31; F,4.48.

I.R. (KBr): 3440; 2950; 2550; 1740; 1470; 1410 cm⁻¹.
N.M.R. CDCl3) 80 MHz: δ12.0–11.4 (s,broad, 1H); 7.4–7.0 (m, 3H); 5.7–4.9 (m, 2H); 4.4–2.2 (m, 12H); 2.0–1.3 (m, 6H).

EXAMPLE 19

1-(3,4-dichlorophenyl)acetyl-2-(3-methoxypyrrolidin-1-yl)methyl piperidine diastereoisomeric mixture Prepared as Example No. 1 from 0.9 g (4.53 mmoles) of 2-(3-methoxypyrrolidin-1-yl)methyl piperidine—diast. mix.—,1.11 g (4.98 mmoles) of 3,4-dichloro-

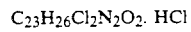

phenylacetyl chloride and 0.68 g (4.98 mmoles) of anhydrous potassium carbonate.

The work-up afforded 1.8 g of the crude product which was purified by silica gel column chromatography as described in Ex.1, obtaining 0.7 g of the title compound as an oil.

$C_{19}H_{26}Cl_2N_2O_2$

M.W.=385.328
I.R. (neat): 3500; 2940; 2800; 1680; 1470; 1445 cm$^{-1}$.
N.M.R. CDCl$_3$) 80 MHz: δ7.4–6.9 (m, 3H); 5.1–4.7 (m, 1H); 4.2–3.7 (m, 3H); 3.6 (s, 2H); 3.2 (s, 3H); 3.0–2.3 (m, 6H); 2.2 (m, 8H).

EXAMPLE 20

1-(4-trifluoromethylphenyl)acetyl-2-(3-methoxypyrrolidin-1-yl) methyl piperidine diastereoisomeric mixture Prepared as Example No. 1 from 0.9 g (4.53 mmoles) of 2-(3-methoxypyrrolidin-1-yl)methyl piperidine—diast. mix.—,1.12 g (4.98 mmoles) of 4-trifluoromethylphenylacetyl chloride and 0.68 g (4.98 mmoles) of anhydrous potassium carbonate.

The work-up afforded 1.9 g of the crude product which was purified by silica gel column chromatography as described in Ex.1, obtained 0.75 g of the title compound as an oil.

$C_{20}H_{27}F_3N_2O_2$

M.W.=384.432
I.R. (neat : 3490; 2940; 2800; 1640; 1450 cm$^{-1}$.
N.M.R. (CDCl$_3$) 80 MHz: δ7.6–7.2 (m, 4H); 5.1–4.6 (m, 1H); 4.1–3.3 (m, 5H); 3.2 (s, 3H); 3.0–2.2 (m, 6H); 2.1–1.1 (m, 8H).

EXAMPLE 21

1-(4-trifluoromethylphenyl)acetyl-2-(3-fluoropyrrolidin-1-yl) methyl piperidine hydrochloride diastereoisomeric mixture Prepared as Example 1, from 0.80 g (4.64 mmoles) of 2-(3-fluoropyrrolidin-1-yl)methyl piperidine—diast. mix.—, 1.19 g (5.34 mmoles) of distilled 4-trifluoromethylphenyl acetyl chloride and 0.78 g (5.65 mmoles) of anhydrous potassium carbonate.

The work-up afforded 1.51 g of the crude product which was purified by silica gel flash column chromatography as described in Example 1.

The purified free base was dissolved in 30 ml of ethyl acetate and the solution brought to acidic pH with HCl/diethyl ether. The precipitate was filtered, washed and dried, to yield 0.93 g of the title compound.

$C_{19}H_{24}F_4N_2O$ .HCl

M.P.=205°–207° C.
M.W.=408.863
I.R. (KBr): 3450; 1630; 1470 cm$^{-1}$.

EXAMPLE 22

1-[1-oxo-3,4-dihydro-(2H)-napht-6-yl]acetyl-2-(3-fluoropyrrolidin-1-yl)methyl piperidine hydrochloride diastereoisomeric mixture Prepared as Example 1, from 0 45 g (2.61 mmoles) of 2-(3-fluoropyrrolidin-1-yl)methyl piperidine—diast. mix.—, 0.76 g (3.43 mmoles) of crude [1-oxo-3,4-dihydro-(2H)-napht-6-yl]acetyl chloride and 0.52 g (3.77 mmoles) of anhydrous potassium carbonate.

The work-up afforded 0.9 g of the crude product which was purified by silica gel flash column chromatography as described in Example 1.

The purified free base was dissolved in 15 ml of acetone and the solution brought to acidic pH with HCl/diethyl ether. The precipitate was filtered, washed and dried, to yield 0.13 g of the title compound.

$C_{22}H_{29}FN_2O_2$.HCl

M.P.=193°–195° C.
M.W.=408.933
I.R. (KBr): 3440; 1680; 1640; 1610; 1420 cm$^{-1}$.
N.M.R. (CDCl$_3$) (80 MHz: δ11.7–12.5 (s broad, 1H); 7.8–8.1 (m, 1H); 7.0–7.3 (m, 2H); 4.8–5.8 (m, 2H); 1.3–4.5 (m, 24H).

EXAMPLE 23

1-(4-trifluoromethylphenyl)acetyl-2-(3-fluoropyrrolidin-1-yl) methyl-3,3-dimethylpiperidine hydrochloride diastereoisomeric mixture Prepared as Example 1, from 0.95 g (4.4 moles) of 2-(3-fluoropyrrolidin-1-yl)methyl-3,3-dimethyl-piperidine—diast. mix.—, 0.88 g (4.84 mmoles) of 4-trifluoromethylphenylacetyl chloride and 0.67 g (4.84 mmoles) of anhydrous potassium carbonate.

The work-up afforded 1.0 g of the crude product which was purified by silica gel flash column chromatography as described in Example 1.

The purified free base was dissolved in 30 ml of acetone and the solution brought to acidic pH with HCl/diethyl ether. The precipitate was filtered, washed and dried, to yield 220 mg of the title compound.

$C_{21}H_{28}F_4N_2O$ .HCl

M.P.=244°–245° C.
M.W.=436.915
I.R. (KBr): 3445; 2950; 1640; 1470 cm$^{-1}$.
N.M.R. (CDCl$_3$): δ11.4–12.5 (s broad, 1H); 7.3–7.7 (m, 4H); 80 MHz 4.6–5.8 (m, 2H); 1.2–4.5 (m, 16H); 0.8–1.20 (s, 6H).

EXAMPLE 24

1-[1-oxo-3,4-dihydro-(2H)-napht-6-yl]acetyl-2-(3-fluoropyrrolidin-1-yl)methyl-3,3-dimethyl piperidine hydrochloride diastereoisomeric mixture Prepared as Example 1, from 1.20 g (5.62 mmoles) of 2-(3-fluoropyrrolidin-1-yl)methyl-3,3-dimethyl-piperidine—diast. mix.—, 1.51 g (6.75 mmoles) of crude [1-oxo-3,4-dihydro-(2H)-napht-6-yl]acetyl chloride and 0.93 g (6.74 mmoles) of anhydrous potassium carbonate.

The work-up of the reaction mixture afforded 2.10 g of the crude product which was purified by silica gel flash column chromatography, eluting with ethyl acetate containing 0.2% of 28% NH$_4$OH.

The purified free base was dissolved in 40 ml of ethyl acetate and the solution brought to acidic pH with HCl/diethyl ether. The precipitate was filtered, washed and dried, to yield 1.15 g of the title compound.

$C_{24}H_{33}FN_2O_2$.HCl

M.P.=198°–207° C.
M.W.=436.985

I.R. (KBr): 3430; 2945; 1680; 1630; 1430 cm$^{-1}$.

EXAMPLE 25

1-[1-oxo-3,4-dihydro-(2H)-napht-6-yl]acetyl-2-(3-fluoropyrrolidin-1-yl)methyl-4,4-dimethyl piperidine hydrochloride diastereoisomeric mixture Prepared as Example 1, from 1.60 g (7.46 mmoles) of 2-(3-fluoropyrrolidin-1-yl)methyl-4,4-dimethyl-piperidine—diast. mix.—, 2.00 g (8.96 mmoles) of crude [1-oxo-3,4-dihydro-(2H)-napht-6-yl]acetyl chloride and 1.23 g (8.96 mmoles) of anhydrous potassium carbonate.

The work-up of the reaction mixture afforded 3.9 go of the crude product which was purified by silica gel flash column chromatography, eluting with ethyl acetate containing 0.3% of 28% NH$_4$OH.

The purified free base was dissolved in 45 ml of ethyl acetate and the solution brought to acidic pH with HCl/diethyl ether. The precipitate was filtered, washed and dried, to yield 1.5 g of the title compound.

$C_{24}H_{33}FN_2O_2.HCl$

M.P.=205°-215° C.
M.W.=436.985
Elemental analysis: Calcd. C, 65.96; H, 7.94; N, 6.41; Cl, 8.11, F, 4,35; Found C, 65.82; H, 7.74; N, 6.19; Cl, 7.88; F, 4.22.
I.R. (KBr): 3420; 2940; 1685; 1625; 1605; 1430 cm$^{-1}$.

EXAMPLE 26

(2S)-1-[1-oxo-3,4-dihydro-(2H)-napht-6-yl]acetyl-2-[(3S)-fluoropyrrolidin-1-yl]methyl piperidine hydrochloride Prepared as Example 1, from 2.06 g (11.06 mmoles) of (2S)-[(3S)-fluoropyrrolidin-1-yl]methyl piperidine, 2.97 g (13.27 mmoles) of crude [1-oxo-3,4-dihydro-(2H)-napht-6-yl] acetyl chloride and 1.84 g (13.27 mmoles) of anhydrous potassium carbonate.

The work-up of the reaction mixture afforded 4.4 g of the crude product which was purified by silica gel flash column chromatography eluting with a mixture of AcOEt, MeOH, 28% NH$_4$OH, 50:1.5:0.3 respectively.

The purified free base was dissolved in 40 ml of acetone and the solution brought to acidic pH with HCl/diethyl ether. The precipitate was filtered, washed and dried, to yield 1.9 g of the title compound.

$C_{22}H_{29}FN_2O_2.HCl$

M.P.=195°-197° C.
M.W.=408.933
$[\alpha]_D^{20}=-48.5$ (C=1, MeOH).
I.R. (KBr): 3440; 1680; 1640; 1610; 1420 cm$^{-1}$.

EXAMPLE 27

(2S)-1-[1-oxo-3,4-dihydro-(2H)-napht-6-yl]acetyl-2-[(3R)-fluoropyrrolidin-1-yl)methyl piperidine hydrochloride Prepared as Example 1, from 1.60 g (8.59 mmoles) of (2S)-[(3R)-fluoropyrrolidin-1-yl)methyl piperidine, 2.31 g (10.31 mmoles) of crude [1-oxo-3,4-dihydro-(2H)-napht-6-yl]acetyl chloride and 1.42 g (10.33 mmoles) of anhydrous potassium carbonate.

The work-up of the reaction mixture and the chromatographic purification of the free base is described in Example 26.

The purified free base (1.85 g) was dissolved in 30 ml of acetone and the solution brought to acidic pH with HCl/diethyl ether. The precipitate was filtered, washed and dried, to yield 1.58 g of the title compound.

$C_{22}H_{29}FN_2O_2.HCl$

M.P.=191°-193° C.
M.W.=408.933
$[\alpha]_D^{20}=-54.1$ (C=1, MeOH).
I.R. (KRb): 3440; 1680; 1630; 1605; 1410 cm$^{-1}$.

TABLE II

| Example n° | (A)— | R | n | R1 | W | *• | MOLECULAR FORMULA | MELTING POINT (°C.) |
|---|---|---|---|---|---|---|---|---|
| 1 | piperidin-2-yl (N) | -CH$_2$-C$_6$H$_3$(Cl)(Cl) | 1 | H | OH | DIAST. MIX. | $C_{18}H_{24}Cl_2N_2O_2.HCl$ | 218-219 |
| 2 | piperidin-2-yl (N) | -CH$_2$-C$_6$H$_4$-CF$_3$ | 1 | H | OH | DIAST. MIX. | $C_{19}H_{25}F_3N_2O_2.HCl$ | 135-137 |
| 3 | piperidin-2-yl (N) | -CH$_2$-C$_6$H$_3$(Cl)(Cl) | 1 | H | OH | S*, S* | $C_{18}H_{24}Cl_2N_2O_2.HCl$ | 199-200 |

TABLE II-continued $$(A)-COR$$
$$CH_2N\begin{matrix}(CH_2)_n\\ \bullet| R_1\\ W\end{matrix}$$

| Example n° | (A)— | R | n | R1 | W | *• | MOLECULAR FORMULA | MELTING POINT (°C.) |
|---|---|---|---|---|---|---|---|---|
| 4 | N-methylpiperidin-2-yl | —CH$_2$-(3,4-diCl-phenyl) | 1 | H | OH | S*, R• | C$_{18}$H$_{24}$Cl$_2$N$_2$O$_2$.HCl.H$_2$O | 92–94 |
| 5 | 3,3-diMe-N-methylpiperidin-2-yl | —CH$_2$-(4-CF$_3$-phenyl) | 1 | H | OH | DIAST. MIX. | C$_{21}$H$_{29}$F$_3$N$_2$O$_2$.HCl | 238–241 |
| 6 | 3,3-diMe-N-methylpiperidin-2-yl | —CH$_2$-(3,4-diCl-phenyl) | 1 | H | OH | DIAST. MIX. | C$_{20}$H$_{28}$Cl$_2$N$_2$O$_2$.HCl | 215–218 |
| 7 | 4,4-diMe-N-methylpiperidin-2-yl | —CH$_2$-(3,4-diCl-phenyl) | 1 | H | OH | DIAST. MIX. | C$_{20}$H$_{28}$Cl$_2$N$_2$O$_2$.HCl.½H$_2$O | 163–166 |
| 8 | N-methylpiperidin-2-yl | —CH$_2$-(3,4-diCl-phenyl) | 1 |  | O | RACEMATE | C$_{18}$H$_{22}$Cl$_2$N$_2$O$_2$.HCl | 213–214 |
| 9 | N-methylpiperidin-2-yl | —CH$_2$-(3,4-diCl-phenyl) | 1 | CH3 | OH | DIAST. A RACEMATE | C$_{19}$H$_{26}$Cl$_2$N$_2$O$_2$.HCl | 174–176 |
| 10 | N-methylpiperidin-2-yl | —CH$_2$-(3,4-diCl-phenyl) | 2 | H | OH | DIAST. MIX. | C$_{19}$H$_{26}$Cl$_2$N$_2$O$_2$.HCl | 205–207 |
| 11 | N-methylpiperidin-2-yl | —CH$_2$-(3,4-diCl-phenyl) | 2 |  | O | RACEMATE | C$_{19}$H$_{24}$Cl$_2$N$_2$O$_2$.HCl | 214–216 |
| 12 | N-methylpiperidin-2-yl | —CH$_2$-(3,4-diCl-phenyl) | 2 | CH3 | OH | DIAST. MIX. | C$_{20}$H$_{28}$Cl$_2$N$_2$O$_2$ | oil |
| 13 | N-methyl-1,2,3,4-tetrahydroisoquinolin-1-yl | —CH$_2$-(3,4-diCl-phenyl) | 1 | H | OH | DIAST. MIX. | C$_{22}$H$_{24}$Cl$_2$N$_2$O$_2$.HCl | 215–217 |

TABLE II-continued structure: (A)—COR with CH2N, (CH2)n, R1, W substituents

| Example n° | (A)— | R | n | R1 | W | *• | MOLECULAR FORMULA | MELTING POINT (°C.) |
|---|---|---|---|---|---|---|---|---|
| 14 | 4,4-dimethyl-N-methyl-1-methyl-tetrahydroisoquinoline | —CH2—C6H3(Cl)(Cl) (3,4-diCl) | 1 | H | OH | DIAST. MIX. | C24H28Cl2N2O2·HCl | 284–286 |
| 15 | N-methyl-1-methyl-tetrahydroisoquinoline | —CH2—C6H3(Cl)(Cl) | 2 | H | OH | DIAST. A RACEMATE | C23H26Cl2N2O2·HCl | 210–214 |
| 16 | N-methyl-1-methyl-tetrahydroisoquinoline | —CH2—C6H3(Cl)(Cl) | 2 | H | OH | DIAST. B RACEMATE | C23H26Cl2N2O2·HCl | 222–224 |
| 17 | 2-methylpiperidine | —CH2—(tetralone) | 1 | H | OH | DIAST. MIX. | C22H30N2O3·HCl | 192–193 |
| 18 | 2-methylpiperidine | —CH2—C6H3(Cl)(Cl) | 1 | H | F | DIAST. MIX. | C18H23Cl2FN2O·HCl | 237–240 |
| 19 | " | " | 1 | H | OCH3 | DIAST. MIX. | C19H26Cl2N2O2 | oil |
| 20 | " | —CH2—C6H4—CF3 | 1 | H· | OCH3 | DIAST. MIX. | C20H27F3N2O2 | oil |
| 21 | " | " | 1 | H | F | DIAST. MIX. | C19H24F4N2O·HCl | 205–207 |
| 22 | " | —CH2—(tetralone) | 1 | H | F | DIAST. MIX. | C22H29FN2O2HCl | 193–195 |
| 23 | 3,3-dimethyl-2-methyl-N-methylpiperidine | —CH2—C6H4—CF3 | 1 | H | F | DIAST. MIX. | C21H28F4N2O·HCl | 244–245 |
| 24 | " | —CH2—(tetralone) | 1 | H | F | DIAST. MIX. | C24H33FN2O2·HCl | 198–207 |

TABLE II-continued

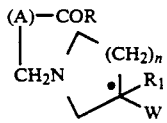

| Example n° | (A)— | R | n | R1 | W | *● | MOLECULAR FORMULA | MELTING POINT (°C.) |
|---|---|---|---|---|---|---|---|---|
| 25 | CH₃/CH₃ piperidine with methyl | " | 1 | H | F | DIAST. MIX. | $C_{24}H_{33}FN_2C_2 \cdot HCl$ | 205–215 |
| 26 | piperidine | " | 1 | H | F | S*, S● | $C_{22}H_{29}FN_2O_2 \cdot HCl$ | 195–197 |
| 27 | " | " | 1 | H | F | S*, R● | $C_{22}H_{29}FN_2O_2 \cdot HCl$ | 191–193 |

The pharmacological activity of the compounds of this invention is illustrated by various in vitro and in vivo models, using the following test procedures, in which the mousetail flick test demonstrates analgesic activity. The results are summarised in Table (III).

PHARMACOLOGICAL TESTS

A) P-phenylquinone-induced abdominal writhing rest in mice

The methodology employed is based on that described by Sigmund et al, Proc. Soc. Exptl. Biol. 95, 729/1957, modified by Milne and Twomey, Agents and Actions, 10, 31/1980.

Male Charles River mice (Swiss Strain), 25–36 g body weight, were used. Animals were allowed food and water ad libitum and were randomized into groups of 10 prior to experimentation. Test compounds were dissolved in either distilled water or distilled water plus 0.1 M AMS, and administered by the subcutaneous route in a final volume of 10 ml/Kg. Control animals received 10 ml/Kg of the appropriate vehicle alone. Following a pretreatment period of 20 min., mice were injected intraperitoneally with p-phenylquinone, 2 mg/Kg at 37° C. in a final volume of 10 mg/Kg. Next, the mice were placed, in groups of 3, in a compartmented perspex box maintained at room temperature and were observed for a period of 8 min. During this period the number of abdominal writhing responses per animal were recorded where writhing consists of an intermittent contraction of the abdomen associated with hind leg extension.

The degree of antinociceptive protection afforded by the test co mound was determined as the mean number of writhing responses observed in the treated group (T) expressed as a percentage of the mean number of writhing response in the control group (C) according to the following formula:

$$[1-(T/C) \times 100\% = \% \text{ graded protection}$$

B) Tail-flick test in mice

The methodology employed is based on that described by D'Amour and Smith, J. Pharmacol. Exp. Ther. 72, 74/1941.

Males Charles River mice (Swiss Strain), 22–34 g body weight were used. Animals were allowed food and water ad libitum and were randomized into groups of 10 prior to experimentation. Before administration of the test compound, the reaction time of each animal was determined by focusing a beam of light onto the tail, exciting a reflex withdrawal after a certain latency; only mice exhibiting a latency between 3–8 sec. were used subsequently in the evaluation of drug effects.

Test compounds were dissolved in either distilled water or distilled water plug 0. 1M AMS and administered by the subcutaneous route in a final volume of 10 ml/Kg. Control animals received 10 ml/kg of the appropriate vehicle alone. Following a pretreatment period of 30 min., the mice were again placed under the heat source and the reaction tine re-determined.

Percentage quantal protection was determined as the number of mice in which the reaction time was doubled compared to pretreatment values, expressed as a percentage of the total number of mice in the group. The results are summarised in Table (III).

TABLE III

| | ANALGESIA | | DURATION OF ACTION | |
|---|---|---|---|---|
| EXAMPLE NO. | MOUSE WRITHING ED50 mg/kg sc | MOUSE TAIL-FLICK ED50 mg/kg sc | M. TAIL-FLICK GRADED % ACTIVITY AT MTFQ ED50 | |
| | | | 30' | 90' |
| 5 | 0.089 | 0.225 | 78 | 82 |
| 6 | 0.081 | 0.233 | 87 | 100 |
| 7 | 0.037 | 0.250 | 84 | 74 |
| 9 | — | 10 mg = 40% | — | — |

TABLE III-continued

| EXAMPLE NO. | ANALGESIA | | DURATION OF ACTION | |
|---|---|---|---|---|
| | MOUSE WRITHING ED50 mg/kg sc | MOUSE TAIL-FLICK ED50 mg/kg sc | M. TAIL-FLICK GRADED % ACTIVITY AT MTFQ ED50 | |
| | | | 30' | 90' |
| 14 | 0.087 | 0.898 | 93 | 85 |
| 17 | 1.784 | 3.238 | 78 | 80 |
| 18 | 0.002 | 0.021 | 80 | 34 |
| 19 | — | 10 mg = 80% | — | — |
| 20 | — | 10 mg = 80% | — | — |
| 22 | 0.005 | 0.065 | 75 | 40 |
| 23 | 0.003 | 0.005 | 90 | 86 |
| 25 | 0.005 | 0.47 | 74 | 56 |

All data are referred to the free base.

We claim:

1. A compound, or solvate or salt thereof, of formula (I):

wherein

A is

R is $R_1$ is hydrogen, halogen, or $C_{1-6}$ alkyl;
$R_2$ and $R_3$ are hydrogen or $C_{1-6}$ alkyl;
$R_5$ together with $R_4$ forms a —$(CH_2)_2$— group optionally summarized by one or two $C_{1-6}$ alkyl groups;
W is halogen or, when A is gem-dimethyl substituted piperidine, is OH; p1 a is 1 or 2.

2. A compound according to claim 1, in which both W and $R_1$ are attached to the azacyclic ring at the 3-position with respect to nitrogen.

3. A compound according to claim 2, in which W is fluoro and $R_1$ is hydrogen, methyl or fluoro.

4. A compound according to claim 3, in which $R_2$ and $R_3$ are hydrogen or methyl.

5. A compound according to claim 1, in which R has the formula

6. A compound according to claim 1, in which R has the formula

7. A compound selected from:
1-(4-trifluoromethylphenyl)acetyl-2-(3-hydroxypyrrolidin-1-yl)methyl-3,3-dimethyl piperidine;
1-(3,4-dichlorophenyl)acetyl-2-(3-hydroxypyrrolidin-1-yl)methyl-3,3-dimethyl piperidine;
1-(3,4-dichlorophenyl)acetyl-2-(3-hydroxypyrrolidin-1-yl)methyl-4,4-dimethyl piperidine;
1-(3-hydroxypyrrolidin-1-yl)methyl-2-(3,4-dichlorophenyl)acetyl 4,4-dimethyl-1,2,3,4-tetrahydroisoquinoline;
1(3,4-dichlorophenyl)acetyl-2-(3-fluoropyrrolidin-1-yl)methyl piperidine;
1-(4-trifluoromethylphenyl)acetyl-2-(3-fluoropyrrolidin-1-yl)methyl piperidine;
1-(1-oxo-3,4-dihydro-(2H)-naphth-6-yl)acetyl-2-(3-fluoropyrrolidin-1-yl)methyl piperidine;
1-(4-trifluoromethylphenyl)acetyl-2-(3-fluoropyrrolidin-1-yl)methyl-3,3-dimethylpiperidine;
1-(1-oxo-3,4-dihydro-(2H)-naphth-6-yl)acetyl-2-(3-fluoropyrrolidin-1-yl)methyl-3,3-dimethyl piperidine;
1-(1-oxo-3,4-dihydro-(2H)-naphth-6-yl)acetyl-2-(3-fluoropyrrolidin-1-yl)methyl-4,4-dimethyl piperidine;
(2S)-1-(1-oxo-3,4-dihydro-(2H)-naphth-6-yl)acetyl-2-((3S)-fluoropyrrolidin-1-yl)methyl piperidine; and
(2S)-1-(1-oxo-3,4-dihydro-(2H)-naphth-6-yl)acetyl-2-((3R)-fluoropyrrolidin-1-yl)methyl piperidine.

8. A compound according to claim 2 wherein W is hydroxy.

9. A compound according to claim 5 wherein $R_2$ and $R_3$ are methyl.

10. A compound according to claim 5, wherein
W is fluoro;
$R_1$ is hydrogen, methyl or fluoro;
W and $R_1$ are attached to the azacyclic ring at the 3 position with respect to the nitrogen; and
$R_2$ and $R_3$ are hydrogen or methyl.

11. A compound according to claim 6 wherein
W is fluoro;
$R_1$ is hydrogen, methyl or fluoro;
W and $R_1$ are attached to the azacyclic ring at the 3 position with respect to the nitrogen; and
$R_2$ and $R_3$ are hydrogen or methyl.

12. 1-(3,4-dichlorophenyl)acetyl-2-(3-hydroxypyrrolidin-1-yl)methyl-4,4-dimethyl piperidine.

13. A method for treating pain which comprises administering a compound according to claim 1.

* * * * *